United States Patent [19]

Narayanan et al.

[11] Patent Number: 5,597,574
[45] Date of Patent: Jan. 28, 1997

[54] UV PROTECTIVE AQUEOUS EMULSION AND EMULSIFIABLE SOLIDS FOR COSMETIC AND AGRICHEMICAL FORMULATIONS

[75] Inventors: Kolazi S. Narayanan, Palisades Park; Robert M. Ianniello, Oak Ridge; David W. Pritchard, Kinnelon, all of N.J.

[73] Assignee: ISP Investments Inc., Wilmington, Del.

[21] Appl. No.: 128,511

[22] Filed: Sep. 28, 1993

Related U.S. Application Data

[63] Continuation-in-part of Ser. No. 975,811, Nov. 13, 1992, and Ser. No. 17,093, Feb. 12, 1993, Pat. No. 5,425,955.

[51] Int. Cl.$^6$ .............. A61K 7/44; A61K 47/32; A01N 25/24; A01N 25/14
[52] U.S. Cl. .............. 424/401; 424/407; 424/405; 71/64.02; 514/972
[58] Field of Search .............. 514/772.5, 972; 424/80, 64, 407, DIG. 5, 401, 405; 71/64.02

[56] References Cited

U.S. PATENT DOCUMENTS

| | | | |
|---|---|---|---|
| 4,668,666 | 5/1987 | Allan et al. | 514/974 |
| 4,676,977 | 6/1987 | Haus et al. | 424/45 |
| 5,026,540 | 6/1991 | Dixon et al. | 424/60 |
| 5,219,559 | 6/1993 | Kopolow | 424/59 |
| 5,283,229 | 2/1994 | Narayanan | 504/116 |
| 5,380,350 | 1/1995 | Fersch | 504/248 |
| 5,421,121 | 6/1995 | Bestwick et al. | 47/41.01 |
| 5,425,955 | 6/1995 | Narayanan | 424/405 |

*Primary Examiner*—Edward J. Webman
*Attorney, Agent, or Firm*—Marilyn J. Maue; Walter Katz; Joshua J. Ward

[57] ABSTRACT

This invention relates to a sunscreen composition comprising between about 1 and about 40 wt. % of a hydrophobic aromatic compound having extended conjugation in its structure and selected from the group of

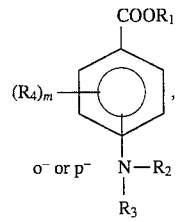

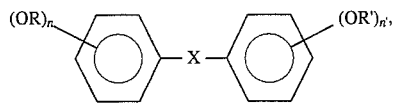

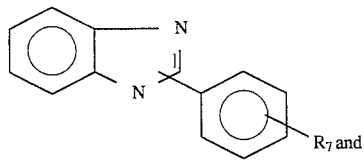

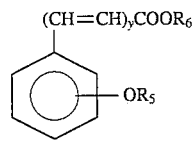

or a mixture of one or more of the above and between about 99 and about 60 wt. % of a film forming water based mixture of from about 12 to about 60 wt. % of a $C_8$ to $C_{14}$ alkyl lactam and mixtures thereof, from about 8 to about 15 wt. % of an Na or K salt of an organic surface active sulfate or sulfonate, from about 5 to about 30 wt. % of a water insoluble $C_{10}$ to $C_{20}$ alpha-olefin/N-vinyl lactam copolymer and from about 15 to about 40 wt. % water, which composition can be added to a cosmetic or agrichemical to stabilize the formulation against UV deterioration.

18 Claims, No Drawings

UV PROTECTIVE AQUEOUS EMULSION AND EMULSIFIABLE SOLIDS FOR COSMETIC AND AGRICHEMICAL FORMULATIONS

This Application is a continuation-in-part of Ser. No. 07/975,811, filed Nov. 13, 1992 copending, and U.S. Ser. No. 08/017,043, filed Feb. 12, 1993, now U.S. Pat. No. 5,425,955 issued Jun. 20, 1995.

In one aspect the invention concerns a non-toxic UV stabilizing, film-forming composition which is readily compatible with commercial cosmetic and agricultural formulations. In another aspect the invention relates to a UV stabilizing water-in-oil concentrate of the composition or to an oil-in-water emulsion of said concentrate. In still another aspect, the invention relates to the dried concentrate in particulate form.

BACKGROUND OF THE INVENTION

Many species of sunscreening agents are employed in the cosmetic art to prevent harmful effects of the sun on the hair and skin or to prevent deterioration of the active agent from UV exposure. However, most sunscreens are easily removed by water or perspiration so that repeated application is needed. While aromatic, water insoluble sun blocks are more resistant to removal, they do not have a high degree of skin, hair or plant substantivity and their incorporation in water based formulations is difficult.

Certain types of polymers exhibit film-forming characteristics and, when dissolved in a suitable solvent, can be applied for the purpose of providing a durable coating on a substrate. Usually, the film-forming polymer solution is applied to a particular substrate and the solvent is allowed to evaporate leaving a film of the polymer. However, such film-forming polymers are generally soluble only in organic solvents which are undesirable for cosmetic and agricultural uses since they possess environmentally adverse properties and are often flammable or otherwise hazardous. Furthermore, the cost of these solvents demands recovery in order to achieve economical operation; however their recovery is not easily realized, usually involving rather complicated and time consuming procedures.

Accordingly, it is an object of this invention to provide an economical and durable sunscreening composition which is non-toxic and has no environmentally adverse affect.

Another object of this invention is to provide a sunscreening concentrate which is readily incorporated into standard cosmetic and agricultural formulations.

Still another object is to provide an oil-in-water emulsion of the present sunscreen composition which is easily combined with cosmetic or agrichemical emulsions or dispersions for their stabilization against the harmful effects of UV light.

Yet another object of this invention is to provide a sunscreening composition in the form of a water-dispersible powder.

THE INVENTION

In accordance with this invention, there is provided a composition of a film-forming water based mixture and an active, hydrophobic UV component which is a non-toxic aromatic compound having extended conjugation in its structure and a UV absorption in the range of 260–400 nm with a maximum absorption above 290 nm. Such active UV screening compounds are defined as having a formula selected from the group of

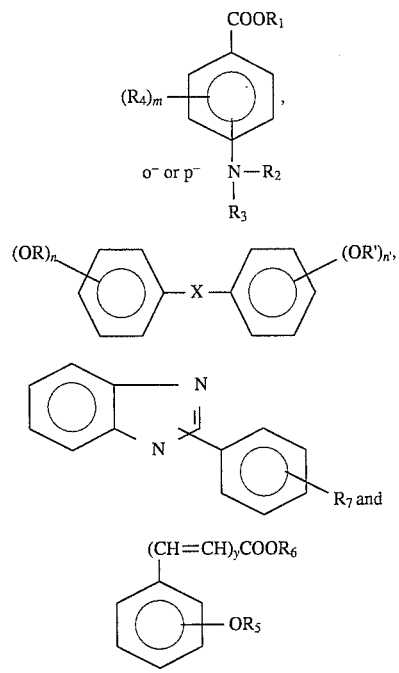

or a mixture of one or more of the above sunscreening agents wherein R and R' are individually hydrogen or $C_1$ to $C_4$ alkyl with the proviso that at least one of R and R' is hydrogen in the o- or p- position of the aromatic ring and another of R and R' is $C_1$ to $C_4$ alkyl also in the o- or p- position of the ring;

$R_1$ is hydrogen or linear, branched or cyclic $C_1$ to $C_{18}$ alkyl or the corresponding metal or amine salt thereof, preferably $C_5$ to $C_8$ alkyl;

$R_2$ and $R_3$ are individually $C_1$ to $C_4$ alkyl;

$R_4$ is hydrogen, $C_1$ to $C_4$ alkyl or alkoxy;

$R_5$ is hydrogen $C_1$ to $C_4$ alkyl and $OR_5$ is in the o- or p- position of the aromatic ring;

$R_6$ is $C_5$ to $C_{10}$ alkyl or an organic salt thereof, preferably an amine salt, most preferably a trialkanol amine salt;

$R_7$ is a sulfonic acid group or a metal or amine salt thereof;

m has a value of from 0 to 3;

n and n' each has a value of from 0 to 2;

X is —CO— when n or n' have a positive value or is

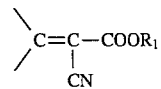

when the sum of n and n' is 0 to 2 and y has a value of from 0 to 1.

Suitable sunscreening agents include phenyl benzimidazole sulfonates, octocrylene, digolloyl trioleate, octyl dimethyl p-amino benzoic acid, octyl methoxy cinnamate, benzophenones, etc. Preferred sunblock agents are 2-hydroxy-4-methoxy benzophenone (ESCOLOL 567), N,N-dimethyl-p-aminobenzoic acid, 2-ethylhexyl-p-dimethylamino benzoate, octyl methoxy cinnamate (ESCALOL 557), octocrylene, digalloyl trioleate, N,N-dimethyl methyl anthranilate, octyl dimethyl p-aminobenzoic acid (ESCALOL 507)

and octyl salicylate (ESCALOL 505). Most preferred are the ESCALOL sunscreen agents supplied by ISP Van Dyk.

The film-forming concentrate medium is a water based mixture of between about 12 and about 60 wt. % of a $C_8$ to $C_{14}$ alkyl lactam or a mixture thereof; between about 8 and about 15 wt. % of a Na or K salt of an organic surface active sulfate or sulfonate; between about 5 and about 30 wt. % of a water insoluble $C_{10}$ to $C_{20}$ α-olefin/N-vinyl lactam copolymer, preferably 40:60–60:40 copolymer; between 0 and about 20 wt. % N-methyl pyrrolidone and between about 15 and about 40 wt. % water. Such film-forming mixture concentrates are described in my copending U.S. patent applications, Ser. No. 975,811 and Ser. No. 017,093, the teachings of which are incorporated herein by reference. Preferred film-forming mixtures employed in the present composition are commercially available AGRIMAX®3, AGRIMAX® 4 and AGRIMAX® 5 supplied by International Specialty Products having the compositions shown below.

| Ingredients | AGRI-MAX® 3 | AGRI-MAX® 4 | AGRI-MAX® 5 |
|---|---|---|---|
| Alcasurf CA (Ca dodecyl benzene sulfonate containing propylene glycol, butanol and aromatics) | 0 | 6.5 | 0 |
| N-octylpyrrolidone | 45.65 | 14.6 | 16.18 |
| N-dodecylpyrrolidone | 0 | 0 | 10.52 |
| N-methylpyrrolidone | 0 | 0 | 16.18 |
| Na dodecylsulfate | 11.39 | 0 | 10.76 |
| Agrimer AL 25 or Agrimer AL 30 | 15.00 | 14.6 | 20.0 |
| Water | 27.96 | 0 | 26.37 |
| Exxon Aromatic 150 (petroleum distillate boiling at 184–205° C. containing alkyl naphthalenes) | 0 | 64.3 | 0 |

In the above concentrate mixture, the film-forming AGRIMER® copolymers, supplied by International Specialty Products, are most preferred. These copolymers include

| | |
|---|---|
| Agrimer AL 25 | copolymer of vinylpyrrolidone and $C_{16}$ α-olefin in 50/50 weight ratio with a number average molecular weight of about 9500; |
| Agrimer AL 30 | graft copolymer containing 80% by weight of $C_{20}$ α-olefin and 20% by weight of polymerized vinylpyrrolidone with a number average molecular weight of about 8600 available as a solid; |
| Agrimer AL 22 | graft copolymer containing 80% by weight of $C_{16}$ α-olefin and 20% by weight of polymerized vinylpyrrolidone with a number average molecular weight of about 7300 available as a liquid; |
| Agrimer VA3 | copolymer containing 30 mole % vinylpyrrolidone units and 70 mole % vinylacetate unit with a number average molecular weight of 5700 and weight average molecular weight of 28,800 determined by the GPC method; |
| Acrylidone ACP-1004 | copolymer containing 50:50 weight ratio of acrylic acid and vinyl pyrrolidone monomers with number average molecular weight = 30,000–60,000, 100,000–300,000. |

An important consideration in the preparation of a drug, cosmetic or agricultural coating composition involves not only a lasting adhesion to the substrate but also prevention of active chemical deterioration due to sunlight. The present water-in-oil concentrates and their oil-in-water emulsions provide this dual protection when incorporated as a carrier for a germicide, medicinal salve, cosmetic cream or spray or agrichemical such as a fertilizer, pesticide, insecticide, fungicide, nutrient, plant growth regulant, herbicide, nematocide, fumigant, insecticidal virus and similar compositions which are adversely affected by sunlight.

The concentration of the UV screening agent in the present film-forming concentrate mixture is between about 1 and about 40 wt. %, preferably between about 2 and about 30 wt. % and most preferably between 5 and 10 wt. %, in a water-in-oil, single phase emulsion. The water-in-oil single phase concentrate may be used directly as a sun block or it can be diluted with water to a stable oil-in-water emulsion, preferably an oil-in-water single phase microemulsion, thickened with an inert thickening agent such as a hydroxy alkyl cellulose, e.g. Klucel H; carbopols (acrylates/acrylic acid crosslinked copolymers; STABILEZE® (maleic acid/methyl vinyl ether copolymers crosslinked with a $C_6$ to $C_{18}$ diene; maleic anhydride/alkyl vinyl ether copolymerized with a $C_8$–$C_{18}$ alkyl ester of methacrylic acid and the like. Also the concentrate can be employed in combination with an appropriate filler such as urea, a water soluble carbohydrate, silica, corn cob particles, bentonite, alumina, talc, diatomaceous earth or other clays, and dried to a particulate solid.

The present concentrates can be diluted with from about 10 to about 1,000 parts water under constant agitation to produce clear, single phase, stable emulsions preferably stable microemulsions which are resistant to separation over an extended period of use. These emulsions, when combined with an agrichemical and applied to plant leaves, seeds or soil, not only resist water wash off and leaching into the surrounding site of application but also prevent light degradation of the active ingredient. The emulsions are also compatible with cosmetic dispersions, suspensions, emulsions, lotions and other formulations to provide products which resist removal by moisture or perspiration and thus afford a more lasting effect, thus eliminating the need for frequent application to the skin or hair.

Optional additives to the concentrate or to the diluted concentrate can be incorporated in an amount up to about 8 wt. % of the concentrate composition. These optional additives include a preservative such as bronopol, an ester of a lower alkanol and p-hydroxybenzoic acid, e.g. p-hydroxy methylbenzoate; a dispersing agent such as an organic silicone, e.g. dimethicone, dimethicone polyol, EO/PO deactivated organic silicones; ethoxylated glyceryl stearate; an active drug; an anionic surfactant such as an alkyl benzene sulfonate, an alkyl aryl phosphate, ethoxylated derivatives thereof, etc. as disclosed in U.S. patent application, Ser. No. 017,093 or any of the standard coloring or flavoring agents for cosmetic use. Agrichemicals, including those indicated in U.S. patent application Ser. No. 017,093 (supra), also can be protected against light degradation. Between about 2 and about 50 wt. %, preferably 10–40 wt. % and most preferably 15–20 wt. % of the present concentrate can be added to a conventional formulation containing a biologically active substance such as an agrichemical, drug or cosmetic formulation which is subject to degradation by exposure to UV light.

The present concentrate containing the active sunscreen ingredient, with the addition of the solid bioactive agent or formulation, can be dried to a powder by any conventional method including fluid bed drying, freeze drying, spray or air drying, freeze drying being preferred. The drying process insures intimate contact and uniform distribution of the UV screening agent and film forming media which can function as a carrier in a cosmetic or agrichemical formulation. Further, the particulate form is more environmentally acceptable and economical since shipping and storage volume is greatly reduced.

Still another alternative in the use of the present sunscreen concentrate involves its introduction into the fermentation process of naturally occurring light sensitive bacterial substances. Examples of such bacterial substances include *bacillus thuringiensis* strains, dibeta thuringiensin, spores of *bacillus popilliae*, grasshopper spore (NOLOC), granulosis virus of codling moth larvae, *bacillus sphaericus,* spores of *verticillium lecanii* fungus, naturally occurring entomogenous nematodes and milled larvae of neodipron (Virox). Pesticides and insecticides which are degraded by exposure to sunlight and which are benefited by incorporation of the sunscreen concentrate include organophosphates and thiophosphates, e.g. chlorpyrifos 0,0-diethyl-0-(3,5,6-trichloro-2-pyridyl phosphorothioate; chlorpyrifos-methyl-0,0-dimethyl-0-(3,5,6-trichloro-2-pyridyl) phosphorothioate; 0,0-diethyl-0-(2-isopropyl-6-methyl-5-pyrimidinyl) phosphorothioate (DIAZINON); tetrahydro-5,5-dimethyl-2(1H) -pyrinidinoine[3-(4-trifluoromethyl)phenyl]-1-[2-(4-trifluoromethyl)phenyl)ethenyl] propenylidene hydrazone (AMDRO) and gamma-1,2,3,4,5,6-hexachlorocyclohexane (LINDANE).

Having thus described the invention, reference is now had to the accompanying examples which illustrate preferred embodiments but which are not to be construed as limiting to the scope of the invention as more broadly defined above and in the appended claims.

EXAMPLE 1.

Preparation of Concentrates Containing UV Protectants

In a one ounce stoppered bottle, 9 g. of Agrimax 3 was mixed with 1 g. of Escalol 567 (2-hydroxy-4-methoxy benzophenone. The mixture was agitated with an orbital stirrer for a period of 2 hours. The resulting composition was clear homogeneous single phase yellow solution. No crystals or oil drops were seen when examined through a microscope at 200× magnification.

EXAMPLE 2

Example 1 was repeated except that Escalol 567 was replaced with Escalol 507 (ethylhexyl dimethyl p-amino benzoate). A clear homogeneous single phase was obtained instantaneously on mixing the components. No crystal or oil drops were seen, when examined through a microscope at 200× magnification.

EXAMPLE 3

Example 2 was repeated except that Escalol 507 was replaced with 3 g. of Escalol 557 (ethylhexyl-p-methoxy cinnamate) and 7 g. Agrtmax 3 in the place of 9 g. was used. A homogeneous single phase microemulsion was thus prepared, containing about 30% of the water insoluble UV active component and about 10% of the water insoluble polymer, both solubilized in 19.5% water. More specifically, the resulting product had the following composition

| Component | | wt. % |
|---|---|---|
| N-octylpyrrolidone | | 32 |
| Na lauryl sulfate | | 8 |
| Escalol 557 | | 30 |
| Agrimer AL 25 (as solid) | | 10.5 |
| Water | | 19.5 |
| | Total | 100.00% |

EXAMPLE 4

Example 2 was repeated replacing Escalol 507 with octocrylene. A clear homogeneous single phase solution was produced upon mixing for 15 minutes. Thus, 10% octocrylene and 13.5% water insoluble polymer (Agrimer AL 25) were solubilized in an aqueous system containing 25% water. Product of the above homogeneous, single phase system had the following composition

| Component | | wt. % |
|---|---|---|
| N-octylpyrrolidone | | 41.0 |
| Na lauryl sulfate | | 10.2 |
| Octocrylene | | 10.3 |
| Agrimer AL 25 (as solid) | | 13.5 |
| Water | | 25.0 |
| | Total | 100.00% |

Examples 1 through 4 illustrate the formulation of single phase concentrates containing UV active water insoluble products aqueous microemulsions to provide a solution of the film forming water insoluble polymer.

EXAMPLE 5

Compositions of Examples 1 and 2, were each mixed with deionized water at the following dilutions 1/10, 1/50 and 1/100 (concentrate/water). In each case stable emulsions with particle size less than 1 μ were produced. The particle size distribution in the above emulsions remained essentially unaltered after storage for more than 1 week.

EXAMPLES 6–9

Following concentrates were prepared according to the procedure in Example 1.

| | |
|---|---|
| Ex. 6 | Escalol 557 (ethyl hexyl p-methoxy cinnamate) 10 wt. % in 90 wt. % of Agrimax 3. |
| Ex. 7 | 5% octocrylene in 95 wt. % Agrimax 3. |
| Ex. 8 | 4.6 wt. % Escalol 557 and 5.8 wt. % octocrylene in 89.6 wt. % Agrimax 3. |
| Ex. 9 | 4.5% Escalol 507 and 3.7 wt. % Escalol 567 in 91.8 wt. % Agrimax 3. |

In each case a single phase homogeneous concentrate composition was obtained.

EXAMPLE 10

Compositions 6–9 were diluted with deionized water at the following levels: 1/10, 1/50 and 1/100. The diluted samples each had particle size averaging less than 0.7 microns in an aqueous dispersion after storage for 2 weeks. In the case of Example 7 (5 wt. % octocrylene in Agrimax 3) at 1/10 dilution to 0.5 wt. % octocrylene, a microemulsion with particle size of from 0.01 to 0.03 microns was obtained.

EXAMPLE 11

A homogeneous composition was prepared using 10 g. of water soluble triethanolamine salt of salicyclic acid and 90 g. Agrimax 3. This composition was thickened by using 0.5% Klucel H to form a gel-like product concentrate.

EXAMPLE 12

A microemulsion composition containing 0.5 wt. % octocrylene, 9.5 wt. % Agrimax 3 and 90 wt. % water was thickened into a gel by the addition of from 0.3 to 0.8 wt. % of a thickening agent such as Klucel H, STABILEZE ACP or Carbopol. The gel format can be used directly, without dilution as a UV protective coating.

EXAMPLE 13

The composition of Example 6 was mixed with talc in the ratios 25:75 and 50:50 and the resulting suspensions were freeze-dried to produce a free-flowing powder for use as a sunscreen.

EXAMPLES 4–17

Incorporation of UV Protecting Concentrate in a Particulate Pesticide

The following general procedure was adopted to prepare compositions 14, 15, 16 and 17 using increasing amounts of the composition of Example 2 containing 10% of the UV protecting agent, thus resulting in an increasing amount of the UV protecting agent. Commercial BT (Bacillus Thuringiensis strain EG 2348) was mixed with the composition of Example 2 (10 wt. % Escalol 507 in Agrimax 3) and slurried with 150 g deionized water. The slurry was freeze-dried at 10° C. over a period of 1 day producing a tan colored powder.

The resulting powders were analyzed for the Escalol 507 content by extraction in ethanol and monitoring the UV spectral data via absorbance at $\lambda max=310$ nm. The results of initial proportions of BT, UV protectant in the composition and the theoretical and actual UV protectant in the products are shown in the following Table

TABLE

| Sample | BT wt. % | Composition of Ex. 2 wt. % | wt. % Escalol 507 in the Final Powder | |
|---|---|---|---|---|
| | | | Theoretical | Actual via Analytical Determination |
| 14 | 47.5 | 2.5 | 0.51 | 0.54 |
| 15 | 45.0 | 5.0 | 1.03 | 1.08 |
| 16 | 40.0 | 10.0 | 2.10 | 2.30 |
| 17 | 50.0 | 50.0 | 5.72 | 5.80 |

Composition of Example 16 was evaluated for biological activity against the standard BT after exposure to sunlight. The radiation dose was equivalent to 12 hours sunlight exposure. Composition 16 showed increased biological activity (20–50%) compared to standard. Examples 14, 15 and 17 also showed increased biological activity of at least 10% over the standard.

EXAMPLE 18

A. Granulosis virus of codling moth larvae was sprayed onto citrus leaves of a live plant infested with codling moth population as a control.

B. In a duplicate experiment, the composition of Example 9 was diluted with 50 parts of water per part of concentrate and the resulting composition, (containing Escalol 507, 0.09 wt. % and Escalol 567, 0.074 wt. %) was sprayed on live citrus leaves immediately after the above treatment with virus and the treated and untreated citrus plants were then exposed to direct sunlight for 6 hours. The plants treated with UV protectant compositions in part B were free from infestation, whereas the plants of part A showed insects survival at 50%.

EXAMPLE 19

Commercial chloropyriphos WDG (80 parts) as water dispersible granules was slurried with an aqueous 20 part mixture of a composition containing 5 wt. % Escalol 507 and 4 wt. % Escalol 567 in 91 wt. % Agrimax 4 and the resulting paste is granulated in an extruder. The wet granules are then dried at 50° C. for a period of 6 hours. These granules are 25% more biologically effective than the commercial WDG after 4 hours exposure to sunlight.

What is claimed is:

1. A stable, film-forming concentrate composition which is resistant to deterioration by UV exposure containing (a) from about 60 to about 99 wt. % of a water insoluble, film-forming mixture comprising between about 12 and about 60 wt. % of a $C_8$ to $C_{14}$ alkyl $C_4$ to $C_6$ lactam or a mixture thereof; between about 8 and about 15 wt. % of a Na, Ca or K salt of an organic surface active sulfate or sulfonate; between about 5 and about 30 wt. % of a water insoluble $C_{10}$ to $C_{20}$ α-olefin/N-vinyl $C_4$ to $C_6$ lactam copolymer; between about 0 and about 20 wt. % of N-methylpyrrolidone and between about 15 and about 40 wt. % water and (b) from about 1 to about 40 wt. % of a water insoluble aromatic compound having extended conjugation and UV absorption in the range of 260–400 nm selected from the group consisting of -continued
(CH=CH)$_y$COOR$_6$

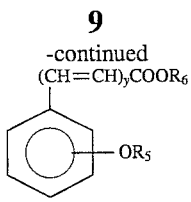

or a mixture of one or more of the above aromatic compounds wherein R and R' are individually hydrogen or C$_1$ to C$_4$ alkyl with the proviso that at least one of R and R' is hydrogen in the o- or p- position of the aromatic ring and another of R and R' is C$_1$ to C$_4$ alkyl also in the o- or p- position of the aromatic ring;

R$_1$ is hydrogen or linear, branched or cyclic C$_1$ to C$_{18}$ alkyl or the corresponding metal or amine salt of —COOR$_1$;

R$_2$ and R$_3$ are individually C$_1$ to C$_4$ alkyl;

R$_4$ is hydrogen or C$_1$ to C$_4$ alkyl or alkoxy;

R$_5$ is hydrogen or C$_1$ to C$_4$ alkyl and OR$_5$ is in the o- or p- position of the aromatic ring;

R$_6$ is C$_5$ to C$_{10}$ alkyl or an organic salt of —COOR$_6$;

R$_7$ is a sulfonic acid group or a metal or amine salt thereof;

m has a value of from 0 to 3;

n and n' each have a value of from 0 to 2;

X is —CO— when n or n' has a positive value or is

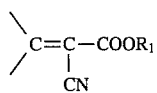

when the sum of n and n' is 0 to 2 and y has a value of from 0 to 1.

2. The composition of claim 1 containing between about 70 and about 98 wt. % of (a) and between about 2 and about 30 wt. % of (b).

3. The composition of claim 2 containing between about 90 and about 95 wt. % of (a) and between about 5 and about 10 wt. % of (b).

4. The composition of claim 1 combined with between about 2 and about 50 wt. % of a formulation containing a light sensitive biologically active agent.

5. The composition of claim 4 wherein said biologically active agent is a bacterial substance of a fermentation process.

6. The composition of claim 4 wherein said biologically active agent is an agrichemical agent.

7. The composition of claim 4 wherein said biologically active agent is a medicinal agent.

8. The composition of claim 4 which is diluted with between about 80 and about 99.9 wt. % of water and from 0 to 5 wt. % of a thickening agent.

9. The composition of claim 1 wherein component (a) comprises a mixture of a N—C$_8$ to C$_{12}$ alkylpyrrolidone; a metal salt of dodecyl sulfonate and a copolymer selected from the group of N-vinylpyrrolidone/α-hexadecyl olefin, N-vinylpyrrolidone/α-eicosyl olefin, N-vinylpyrrolidone/vinyl acetate, N-vinylpyrrolidone/acrylic acid and a mixture of said copolymers.

10. The composition of claim 1 which additionally contains from up to 8 wt. % of an excipient selected from the group of a thickener, a filler, a preservative, a surfactant, a coloring agent and a flavoring agent.

11. The composition of claim 1 in the form of a particulate product.

12. The composition of claim 1 in the form of a dispersion or emulsion.

13. The composition of claim 1 in the form of a paste.

14. The composition of claim 1 wherein said component (b) is selected from the group of 2-hydroxy-4-methoxy benzophenone, octyl methoxy cinnamate, octocrylene, octyl dimethyl-p-amino benzoic acid, octyl salicylate and mixtures thereof.

15. The composition of claim 1 wherein R$_1$ is C$_5$ to C$_8$ alkyl.

16. The composition of claim 1 wherein R$_6$ is C$_5$ to C$_{10}$ alkyl.

17. The composition of claim 16 wherein R$_6$ is C$_5$ to C$_{10}$ trialkanol amine.

18. The composition of claim 16 wherein R$_1$ is C$_5$ to C$_8$ alkyl and R$_6$ is an amine salt of C$_5$ to C$_{10}$ alkyl.

* * * * *